US009194876B2

(12) United States Patent
Tokunga et al.

(10) Patent No.: US 9,194,876 B2
(45) Date of Patent: Nov. 24, 2015

(54) SAMPLE INSPECTION SYSTEM AND OPERATING METHOD FOR MANAGEMENT SERVER THEREOF

(75) Inventors: Tatsuya Tokunga, Tokyo (JP); Naomi Ishii, Mito (JP); Takashi Noguchi, Machida (JP); Masaki Takano, Tokyo (JP); Yayoi Shitara, Musashino (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 635 days.

(21) Appl. No.: 12/729,787

(22) Filed: Mar. 23, 2010

(65) Prior Publication Data

US 2010/0250174 A1 Sep. 30, 2010

(30) Foreign Application Priority Data

Mar. 31, 2009 (JP) .................................. 2009-083964

(51) Int. Cl.
| | |
|---|---|
| G01N 1/28 | (2006.01) |
| G01N 1/02 | (2006.01) |
| G01P 15/16 | (2013.01) |
| G01F 3/00 | (2006.01) |
| G01N 35/00 | (2006.01) |

(52) U.S. Cl.
CPC .................................. *G01N 35/0092* (2013.01)

(58) Field of Classification Search
CPC ............................................. G01N 2001/007
USPC .................. 702/19, 20, 30, 81, 83, 108, 185; 382/128; 600/300; 705/2
See application file for complete search history.

(56) References Cited

U.S. PATENT DOCUMENTS

| 5,461,570 A * | 10/1995 | Wang et al. .................... 700/110 |
| 7,978,890 B2 * | 7/2011 | Yamagishi et al. ........... 382/128 |
| 2005/0038676 A1 * | 2/2005 | Showalter et al. ................ 705/2 |
| 2010/0121156 A1 * | 5/2010 | Yoo ............................... 600/300 |

FOREIGN PATENT DOCUMENTS

JP 11-281652 10/1999

* cited by examiner

*Primary Examiner* — John Breene
*Assistant Examiner* — Felix Suarez
(74) *Attorney, Agent, or Firm* — Baker Botts L.L.P.

(57) ABSTRACT

A management server of a sample inspection system includes sample processing information generated on the basis of inspection request data, facility data, a simulation execution portion and a window generation portion for generating a monitor window. The inspection request data contains a priority, an order time, a required time and inspection items and the sample processing information contains an inspection start time and an inspection estimate finish time. The monitor window has a work area in which the samples represented by sample bars parallel to the abscissa are arranged in a vertical direction and a past record and a future schedule are allocated to this abscissa with the present time as the base. The sample bars display a simulation execution portion for executing simulation on the basis of the inspection start time, the inspection estimate finish time and a delay time. The management server displays the simulation result.

14 Claims, 11 Drawing Sheets

FIG.2A

| PATIENT ID | INSPEC-TION ID | PRIOR-ITY | ORDER TIME | RE-QUIRED TIME | INSPEC-TION ITEM |
|---|---|---|---|---|---|
| — | — | — | — | — | — |

| PATIENT ID | INSPEC-TION ID | SLAVE INSPEC-TION ID | PRIOR-ITY | ORDER TIME | RE-QUIRED TIME | INSPEC-TION ITEM | PRESENT WORK POSITION | START TIME | ESTI-MATE TIME |
|---|---|---|---|---|---|---|---|---|---|
| — | — | — | — | — | — | — | — | — | — |

| FACILITY | CON-VEYOR PATH | BUFFER | PIPETT-ING MODULE | CON-VEYOR PATH | BUFFER | ANA-LYZING MODULE |
|---|---|---|---|---|---|---|
| RE-QUIRED TIME | 1 | 1 | 2 | 1 | 1 | 10 |

| | SAMPLE FLOWING AHEAD HAS LEVEL C | SAMPLE FLOWING AHEAD HAS LEVEL B | SAMPLE FLOWING AHEAD HAS LEVEL A |
|---|---|---|---|
| SAMPLE FLOWING BEHIND HAS LEVEL C | SAMPLES ARE AWAITED IN FLOWING SEQUENCE AND DELAY OCCURS IN SAMPLES FLOWING BEHIND | SAMPLES ARE AWAITED IN FLOWING SEQUENCE AND DELAY OCCURS IN SAMPLES FLOWING BEHIND | SAMPLES ARE AWAITED IN FLOWING SEQUENCE AND DELAY OCCURS IN SAMPLES FLOWING BEHIND |
| SAMPLE FLOWING BEHIND HAS LEVEL B | SAMPLE OF LEVEL C IS OVERRUN AND DELAY OCCURS IN THIS LEVEL C SAMPLE | SAMPLES ARE AWAITED IN FLOWING SEQUENCE AND DELAY OCCURS IN SAMPLES FLOWING BEHIND | SAMPLES ARE AWAITED IN FLOWING SEQUENCE AND DELAY OCCURS IN SAMPLES FLOWING BEHIND |
| SAMPLE FLOWING BEHIND HAS LEVEL A | SAMPLE OF LEVEL C IS OVERRUN AND DELAY OCCURS IN THIS LEVEL C SAMPLE | SAMPLE OF LEVEL B IS OVERRUN AND DELAY OCCURS IN THIS LEVEL B SAMPLE | SAMPLES ARE AWAITED IN FLOWING SEQUENCE AND DELAY OCCURS IN SAMPLES FLOWING BEHIND |

| SAMPLE | LEVEL | CON-VEYOR PATH | BUFF-ER | WAIT-ING | PIPETT-ING | CON-VEYOR PATH | BUFF-ER | WAIT-ING | ANALY-SIS | TOTAL |
|---|---|---|---|---|---|---|---|---|---|---|
| SAMPLE 1 | C | 1 MIN. | 1 MIN. | 0 MIN. | 2 MIN. | 1 MIN. | 1 MIN. | 0 MIN. | 10 MIN. | 16 MIN. |

| SAMPLE | LEVEL | CON-VEYOR PATH | BUFF-ER | WAIT-ING | PIPETT-ING | CON-VEYOR PATH | BUFF-ER | WAIT-ING | ANALY-SIS | TOTAL | DELAY |
|---|---|---|---|---|---|---|---|---|---|---|---|
| SAMPLE 1 | C | 1 MIN. | 1 MIN. | 6 MIN. | 2 MIN. | 1 MIN. | 1 MIN. | 9 MIN. | 10 MIN. | 31 MIN. | +15 MIN. |
| SAMPLE 2 | B | 1 MIN. | 1 MIN. | 2 MIN. | 2 MIN. | 1 MIN. | 1 MIN. | 3 MIN. | 10 MIN. | 21 MIN. | — |
| SAMPLE 3 | C | 1 MIN. | 1 MIN. | 4 MIN. | 2 MIN. | 1 MIN. | 1 MIN. | 9 MIN. | 10 MIN. | 29 MIN. | — |
| SAMPLE 4 | C | — | — | — | — | — | — | 12 MIN. | 10 MIN. | 22 MIN. | — |
| SAMPLE 5 | C | — | — | — | — | — | — | 6 MIN. | 10 MIN. | 16 MIN. | — |
| SAMPLE 6 | B | — | — | — | — | — | — | 3 MIN. | 10 MIN. | 13 MIN. | — |

| SAMPLE | LEVEL | CON-VEYOR PATH | BUFF-ER | WAIT-ING | PIPETT-ING | CON-VEYOR PATH | BUFF-ER | WAIT-ING | ANALY-SIS | TOTAL | DELAY |
|---|---|---|---|---|---|---|---|---|---|---|---|
| SAMPLE 1 | B | 1 MIN. | 1 MIN. | 4 MIN. | 2 MIN. | 1 MIN. | 1 MIN. | 3 MIN. | 10 MIN. | 23 MIN. | +7 MIN. |
| SAMPLE 2 | B | 1 MIN. | 1 MIN. | 2 MIN. | 2 MIN. | 1 MIN. | 1 MIN. | 3 MIN. | 10 MIN. | 21 MIN. | — |
| SAMPLE 3 | C | 1 MIN. | 1 MIN. | 6 MIN. | 2 MIN. | 1 MIN. | 1 MIN. | 9 MIN. | 10 MIN. | 31 MIN. | +2 MIN. |
| SAMPLE 4 | C | — | — | — | — | — | — | 15 MIN. | 10 MIN. | 25 MIN. | +3 MIN. |
| SAMPLE 5 | C | — | — | — | — | — | — | 6 MIN. | 10 MIN. | 16 MIN. | — |
| SAMPLE 6 | B | — | — | — | — | — | — | 3 MIN. | 10 MIN. | 13 MIN. | — |

| SAMPLE | LEVEL | CONVEYOR PATH 1 | BUFFER 1 | WAITING | PIPETTING M | CONVEYOR PATH 2 | BUFFER 2 | WAITING | ANALYSIS 1 | TOTAL | DELAY |
|---|---|---|---|---|---|---|---|---|---|---|---|
| SAMPLE 1 | A | 1 MIN. | 1 MIN. | 0 MIN. | 2 MIN. | 1 MIN. | 1 MIN. | 0 MIN. | 10 MIN. | 16 MIN. | 0 MIN. |
| SAMPLE 2 | B | 1 MIN. | 1 MIN. | 4 MIN. | 2 MIN. | 1 MIN. | 1 MIN. | 3 MIN. | 10 MIN. | 23 MIN. | +2 MIN. |
| SAMPLE 3 | C | 1 MIN. | 1 MIN. | 6 MIN. | 2 MIN. | 1 MIN. | 1 MIN. | 9 MIN. | 10 MIN. | 31 MIN. | +2 MIN. |
| SAMPLE 4 | C | — | — | — | — | — | — | 15 MIN. | 10 MIN. | 25 MIN. | +3 MIN. |
| SAMPLE 5 | C | — | — | — | — | — | — | 12 MIN. | 10 MIN. | 22 MIN. | +6 MIN. |
| SAMPLE 6 | B | — | — | — | — | — | — | 3 MIN. | 10 MIN. | 13 MIN. | — |

SAMPLE INSPECTION SYSTEM AND OPERATING METHOD FOR MANAGEMENT SERVER THEREOF

INCORPORATION BY REFERENCE

The present application claims priority from Japanese application JP2009-083964 filed on Mar. 31, 2009, the content of which is hereby incorporated by reference into this application.

BACKGROUND OF THE INVENTION

This invention relates to a sample inspection system including a plurality of analyzers connected to a conveyor line and an operating method for a management server of the system. More particularly, the invention relates to a sample inspection system that can be applied to a pre-processor for conducting centrifugal separation and pipetting for samples before the start of inspection and to an analyzer for analyzing the components of the sample after the pre-processing is completed and an operating method for a management server of the system.

A sample inspection system including a pre-processor and an analyzer has been introduced in recent years into an inspection room of a hospital to speed up an inspection processing and to quickly report the inspection result to doctors. Urgency requirement levels of the inspection are different among patients such as periodical inspection of hospital patients, inspection of out-patients and inspection of patients under operation and this system makes it possible to quickly report the inspection results of the samples having different requirement levels by assigning priorities corresponding to the requirement levels to the patients. For example, the pre-processor described above satisfies the requirement by preferentially sending out those samples having higher priorities. The technology described in JP-A-11-281652 updates the priority of samples allocated in advance to the pre-processor when it is desired to speed up the pre-processing of a specific sample.

According to the prior art, a display device of a control management portion has a monitor window for the position of a sample and its priority and a priority inputting window and can grasp in which stage of the system a sample having a sample ID and a priority as a pair exists and can easily change and correct the priority. In particular, in the prior art, an operator of the system can easily decide or correct the priority by retrieving a sample having a higher priority than the priority of a sample requiring urgent inspection after confirming the content of the former.

When a large number of samples having high urgency levels are charged, the problem develops quite naturally in that delay of samples having lower priorities becomes great. The prior art technology described above teaches an operating method for increasing the priority of samples with the lapse of time to prevent corrosion of the samples when racks stay for a long time but a sample inspection system has been desired in which the operator can grasp the influences on other samples and can then decide the sample having urgency when deciding the urgent samples.

SUMMARY OF THE INVENTION

It is therefore an object of the invention to provide a sample inspection system capable of executing a preferential processing while taking the priorities of a plurality of samples processed inside the system and their progress into consideration, and an operating method for a management server of the system.

In a sample inspection system and an operating method for a management server of the system for accomplishing the object of the invention described above, the management server of the sample inspection system has sample processing information generated on the basis of inspection request data accepted from a sample access system, facility data having a processing time of the sample inspection line, a simulation execution portion for simulating the processing time of the sample on the basis of the sample processing information and the facility data and a window generation portion for generating a monitor window to be outputted to the monitor device; wherein the inspection request data contains a priority, an order time, a required time and inspection items; wherein the sample processing information contains an inspection start time and an inspection estimate finish time in addition to the information of the inspection request data; wherein the monitor window has a work area for vertically arranging the samples represented by sample bars parallel to the abscissa to which a past record and a future schedule are allocated with the present time as the base and displays the sample bars, the inspection start time, the inspection estimate finish time and the delay time; and wherein the management server displays the simulation result processed by the simulation execution portion on the monitor window.

According to the invention, the result of simulation executed on the basis of the sample processing information of each sample and the facility data of the sample inspection line is displayed as sample bars in a bar graph type that are arranged in a vertical direction on the basis of the past record and the future estimate including the delay information with the present time as the base. Therefore, the overall condition can be grasped more easily.

Other objects, features and advantages of the invention will become apparent from the following description of the embodiments of the invention taken in conjunction with the accompanying drawings.

BRIEF DESCRIPTION OF THE DRAWINGS

FIGS. 2A, 2B and 2C are tables each showing a construction of main data of the sample inspection system according to the invention;

FIG. 3 is a work definition table of priority of the sample inspection system according to the invention;

DESCRIPTION OF THE EMBODIMENTS

A sample inspection system according to an embodiment of the invention will be hereinafter explained concretely with reference to FIG. 1 to FIG. 10.

In the sample inspection system 1a according to this embodiment, priority is assigned to each of a plurality of samples and the inspection can be executed in accordance with this priority. A specific sample is designated from among the plurality of samples (hereinafter called "specific sample") and the change of the priority can be accepted. Therefore, the inspection requirement can be executed in consideration of processing conditions of the plurality of samples.

To begin with, the system construction of this sample inspection system 1a will be explained with reference to FIG. 1. Here, FIG. 1 is a system construction view of the sample inspection system 1a.

Figure 1:
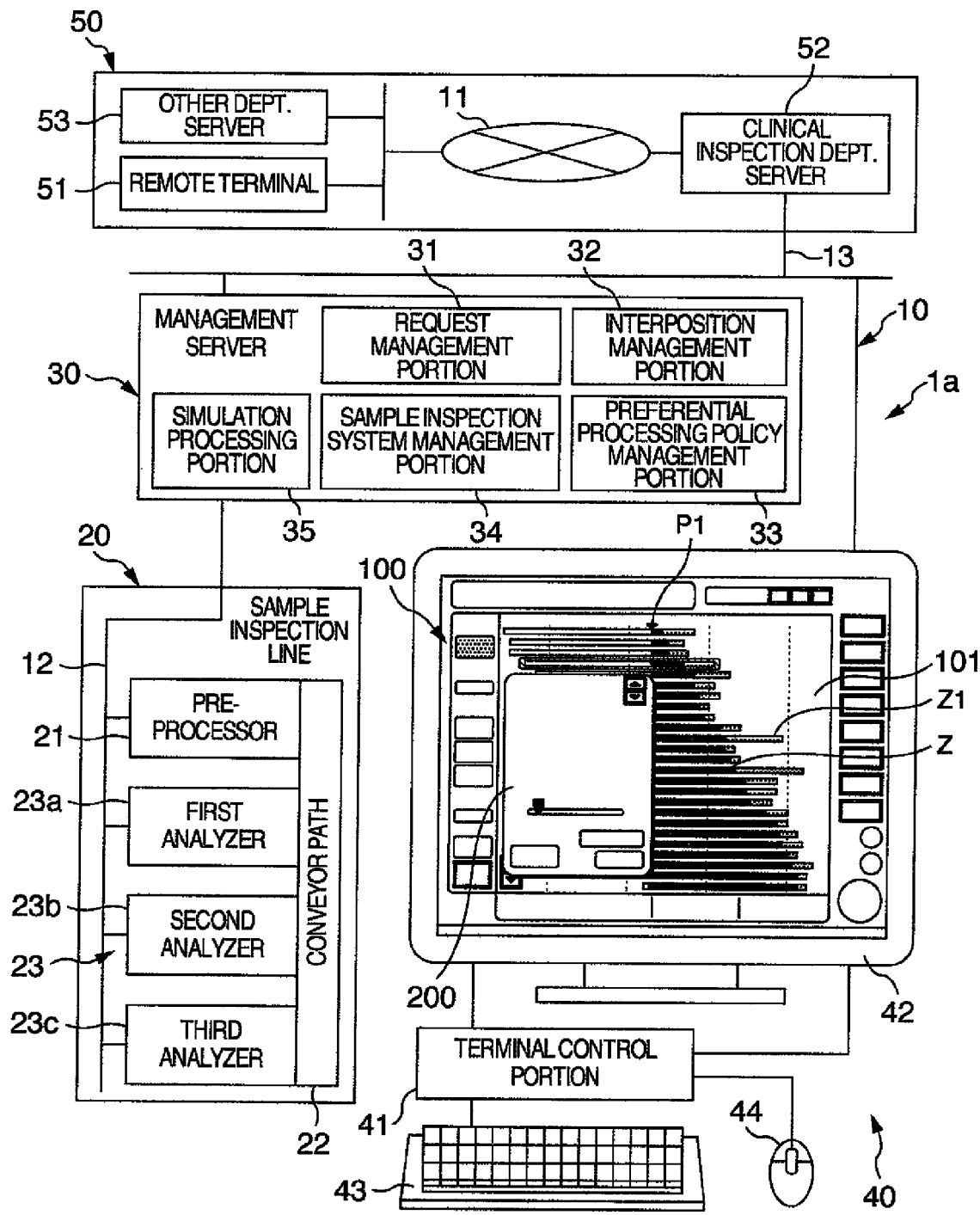
FIG. 1 is a structural view showing a sample inspection system according to an embodiment of the invention.

Referring to FIG. 1, the sample inspection system collectively denoted by reference numeral 1a is configured by connecting, through a network 10, a sample inspection line 20 for analyzing samples, a management server 30 for collectively managing the sample inspection line 20, a local terminal 40 for monitoring the management server 30 and correcting the input and a sample access system 50 for requesting the inspection of the sample.

The sample access system 50 is configured by connecting, through a network 11, a remote terminal 51 for generating a registration request of the sample inspection, a clinical inspection department server 52 for managing registration and result of the clinical inspection, other department server 53 as a server of an X-ray inspection department. The sample inspection line 20 is configured by connecting, through a network 12, a pre-processor 21 for stocking the samples into a test tube, uncorking the test tubes and pipetting the samples into a plurality of slave samples, a conveyor path 22 for taking in and out and conveying the samples and a plurality of analyzers 23 (first, second and third analyzers 23a, 23b and 23c) for analyzing the slave samples.

The management server 30 includes a request management portion 31 for managing a request for the specific sample, an interposition management portion 32 for managing the interposition by an operator, a priority processing policy management portion 33 for managing a priority processing policy for the specific sample, a sample inspection system management portion 34 for managing the processing condition of the sample inspection, a simulation management portion 35 for simulating the processing condition of the samples with the priority processing and a communication portion and a storage device not shown in the drawing. This management server 30 may be composed of one or a plurality of servers.

The local terminal 40 includes a terminal control portion 41 for collectively controlling the local terminal 40, a display device 42 for displaying various kinds of monitor windows about the operation management of the management server 30, and a keyboard 43 and a mouse 44 as input devices. Here, the clinical inspection department server 52, the management server 30 and the local terminal 40 are connected to one another through a network 13.

According to the sample inspection system 1a of this embodiment, a doctor in a consultation room can issue inspection request data 60 (refer to FIG. 2A) of the sample requiring the inspection from the remote terminal 51 to the clinical inspection department server 52. The program stored in the other department server 53 can also issue the inspection request of the sample to the clinical inspection department server 52. The inspection request may further be generated through the interlocking operation of the remote terminal 51 and the other department server 53.

Receiving the inspection request, the clinical inspection department server 52 transmits the inspection request data 60 to the management server 30. The management server 30 receives the inspection request data 60 and stores it in an inspection request DB of the request management portion 31 not shown in the drawing. Next, the management server 30 transmits the inspection request data 60 to the pre-processor 21. The pre-processor 21 carries out the pipette processing of the sample to the slave samples on the basis of the inspection request data and then transmits the set of the sample ID and the slave sample ID and the start time to the management server 30. The management server 30 receives the set of the sample ID and the slave sample ID and the start time and stores them as sample inspection processing data 70 (refer to FIG. 2B) to a sample-wise processing condition management DB of the sample inspection system management portion 34 not shown in the drawing. The management server 30 monitors and controls the sample inspection line 20 so that the inspection can be carried out in accordance with the priority on the basis of the sample-wise processing condition management DB.

One of the great features of the sample inspection system 1a of this embodiment lies in that it can generate the monitor window 100 for bar-displaying the processing condition of each sample and the delay from the required time with the present time P1 as the reference.

In other words, because this embodiment employs the priority, the sample having a higher priority is processing preferentially to a sample having a lower priority whereas a sample having a lower priority is outrun one after another by samples having higher priorities and its processing gets slower and slower. For this reason, the inspection time varies incessantly with the number of samples and their priorities.

In this embodiment, the processing condition of the samples that varies every moment can be outputted to the display device 42 of the local terminal 40 and displayed on the easy-to-grasp monitor window 100. This monitor window 100 is generated by the priority processing policy management portion 33 of the management server 30. The priority processing policy management portion 33 allows the simulation management portion 35 to executes the processing either periodically or appropriately on the basis of the sample-wise processing condition management DB stored in the sample inspection management portion 34 and generates the monitor screen 33 on the basis of the processing result.

The simulation management portion 35 has facility data 80 (refer to FIG. 2C) about the sample inspection line 20 such as the conveying time of the conveyor path 22 and the inspection time of the analyzers 23 and the inspection required time of the individual samples can be calculated by virtually putting the sample processing information 70 stored in sample-wise processing condition management DB into the facility data 80.

In this embodiment, the individual samples are displayed by sample bars Z arranged on the ordinate and are displayed in a work area 101 in which the lapse of time and the estimate are expressed on the abscissa with the present time P1 as the reference. In the case of FIG. 1, for example, the individual samples are displayed vertically by the sample bars Z with the present time P1 at the center as the reference. The lapse of time involved so far is displayed on one of the sides (left) of the present time P1 and the time estimated from now on is displayed on the other side (right). Moreover, the delay time Z1 is displayed distinguishably in the estimate time.

According to this embodiment, the start time and the finish estimate time can be known for each sample and the delay time Z1 can also be known. A condition of whole samples but not an individual sample can be grasped at a look, since a plurality of samples to be displayed by the sample bars Z are displayed in alignment. Incidentally, this embodiment represents the case where the monitor window 100 is displayed by the local terminal 40 but may well be displayed by the remote terminal 51 which is to request the sample inspection. The priority can be decided more easily when the monitor window 100 can be confirmed by the remote terminal 51.

Another great feature of the sample inspection system 1a according to this embodiment is that the sample displayed on the monitor window 100 can be displayed in accordance with the priority or the sample can be the one that has a large inspection required time or the one that has a large delay time. Still alternatively, the samples can be those which are extracted by setting the retrieval condition such as the requesting parties. As a result, the point of trouble having a large delay can be discovered more easily.

Still another great feature of the sample inspection system 1a according to the embodiment is that the change of the priority of the specific sample can be accepted by designating the specific sample on the monitor window 100.

In other words, this embodiment can call the sample processing information 70 corresponding to the sample bars Z stored in the sample-wise processing condition management DB onto the change window 200 displayed in superposition and can correct the information by selecting the sample bars Z representing the individual samples. Consequently, the embodiment can easily change the priority of the samples having a large delay or the priority of urgent samples.

Still another great feature of the sample inspection system 1a of this embodiment is that simulation can be made to grasp the influences of the change of the priority on other samples on the monitor window 100.

In other words, this embodiment can easily change the priority by designating the specific sample. When the priority is changed, however, the change may result in the delay of other samples. The level of the priority to be established is another large problem. When changing the priority, therefore, this embodiment accepts the change of provisional priority of the specific sample, executes simulation on the basis of this provisional priority and reflects the simulation result on the monitor window 100. In this way, the embodiment can set the priority having small influences.

The sample inspection system 1a according to this embodiment will be explained in further detail with reference to FIGS. 2 to 10.

Referring initially to FIG. 2, the main data construction employed by this embodiment will be explained. FIGS. 2A to 2C are main data construction views. FIG. 2A shows the inspection request data 60, FIG. 2B shows the sample processing information 70 and FIG. 2C shows the facility data 80.

Referring to FIG. 2A, the inspection request data 60 contains a patient ID 61, an inspection ID 62, a priority 63, an order time 64, a required time 65 and an inspection item 66. A user using the remote terminal 51 sets the information necessary for the inspection such as the priority 63, the required time 65 and the inspection item 66 to the input window specifying the patient ID 61 and not shown in the drawing. The remote terminal 51 then acquires the inspection ID 62 and the order time 64.

In FIG. 2B, the sample processing information 70 is the sum generated by putting the slave inspection ID 71, the present work position 72, the inspection start time 73 and the estimate time 74 to the inspection request data 60. The slave inspection ID 71, the present work position 72 under operation and the start time 73 that are acquired automatically in the sample inspection line 20 are stored. The estimate time 74 is updated on the basis of the simulation result executed automatically or appropriately in the priority processing policy management portion 33.

In FIG. 2C, the facility data 80 is set by the condition of the facility of the sample inspection line 20 and the processing performance. The explanation given with reference to FIG. 2C is based on the facility data 80 used for explaining the subsequent simulation by way of example. It will be assumed that the sample inspection line 20 is composed of the pre-processor 21 including a buffer 83 and a pipetting module 84 and the analyzer 23 including a buffer 86 and an analyzing module 87, and the conveyor path 82 for conveying the sample to the pre-processor 21 and the conveyor path 85 for conveying the samples from the pre-processor 21 to the analyzer 23 are set to the sample inspection line 20.

This embodiment is based on the following premise. Namely, one minute is necessary as the required time of the conveyor path 82 for conveying the sample to the buffer 83 and another one minute is necessary for the movement of the sample inside the buffer 83. The required time of the pipetting work in the pipetting module 84 is 2 minutes, one minute is necessary as the required time of the conveyor path 85 for moving the sample from the pipetting module 84 to the analyzer 23 and another one minute is necessary for the movement of the sample inside the buffer 86. The required time of the analyzing work of the analyzing module 87 is 10 minutes. This embodiment has the capacity of finishing the sample inspection within the total required time of 16 minutes unless a wait time exists. However, the inspection wait time is necessary in the buffers 83 and 86, since a large number of samples each having a different priority flow in the actual sample inspection work. This wait time is the main delay time.

Incidentally, this embodiment represents a simple case to simplify the explanation. In practice, a large number of analyzers 23 are provided to the sample inspection line 20. In the inside of the pre-processor 21 or the analyzers 23, it is also fractionized into a transmitting time, a wait time, a pipetting time or an analyzing time. This facility data 80 may contain each facility portion and the necessary required time of each facility portion as the basic data.

Next, the priority employed in the sample inspection system 1a in this embodiment and the simulation process involved with the priority will be explained concretely with reference to FIGS. 3 to 7B. FIG. 3 is a work definition diagram of the priority. FIGS. 4A to 7B are simulation process charts corresponding to the priority, FIGS. 4A, 5A, 6A and 7A are flowcharts and FIGS. 4B, 5B, 6B and 7B are required time calculation tables.

In this embodiment, the priority is set to three stages of levels A to C. FIG. 3 defines the relation of each level with the other. The simulation management portion 35 carries out simulation on the basis of this definition by referring to the data acquired from the sample processing information 70.

In FIG. 3, the abscissa represents the levels of the samples flowing ahead and the ordinate does the levels of the samples flowing afterward. This embodiment defines in such a fashion that the level A flows on the sample inspection line 20 with the highest priority, the level B has the next highest priority and the level C does not have the priority. To simplify the explanation, it will be assumed in this embodiment that the change of the sequence of the conveyor path 22 and the pre-processor 21 relative to the work units of the analyzers 23 does not occur but the change of the work sequence corresponding to the priority occurs at the work waiting position such as the buffer. However, the embodiment is not necessarily limited to this example but can also be applied to the process in which outrun is possible.

In FIG. 3, when the sample flowing afterward has the priority of the level C, the work is allowed to proceed in the sequence in which the samples of the level C are charged, irrespective of the priority of the sample flowing ahead. Therefore, the delay due to turn-wait occurs in the sample having the priority of the level C. In contrast, when the sample flowing afterward has the priority of the level B, the sample outruns the sample flowing ahead when the priority of the latter is the level C, and the work is carried out in the sequence of charging when the priority has the levels B and A. Therefore, the delay occurs in the samples having the priority of the level C since it is overrun. When the priorities of the levels B and A exist ahead, the delay occurs in the sample of the level B that flows afterward. When the sample flowing afterward has the priority of the level A, on the other hand, the samples flowing ahead are outrun when their priorities are levels C and B and the work is carried out in the sequence of charging when the priority is the level A. In consequence, the delay occurs in the samples having the priorities of the levels C and B because these samples are outrun. When the level A exists ahead, the delay occurs in the samples flowing afterward even when their priority is the level A.

FIGS. 4A to 7B show the simulation result corresponding to the priority calculated by the simulation management portion 35. Here, FIGS. 4A, 5A, 6A and 7A show the process diagrams of the sample inspection line 20 and FIGS. 4B, 5B, 6B and 7B show the tables representing the simulation result of the samples flowing on the sample inspection line 20.

Figures 4A, 4B:
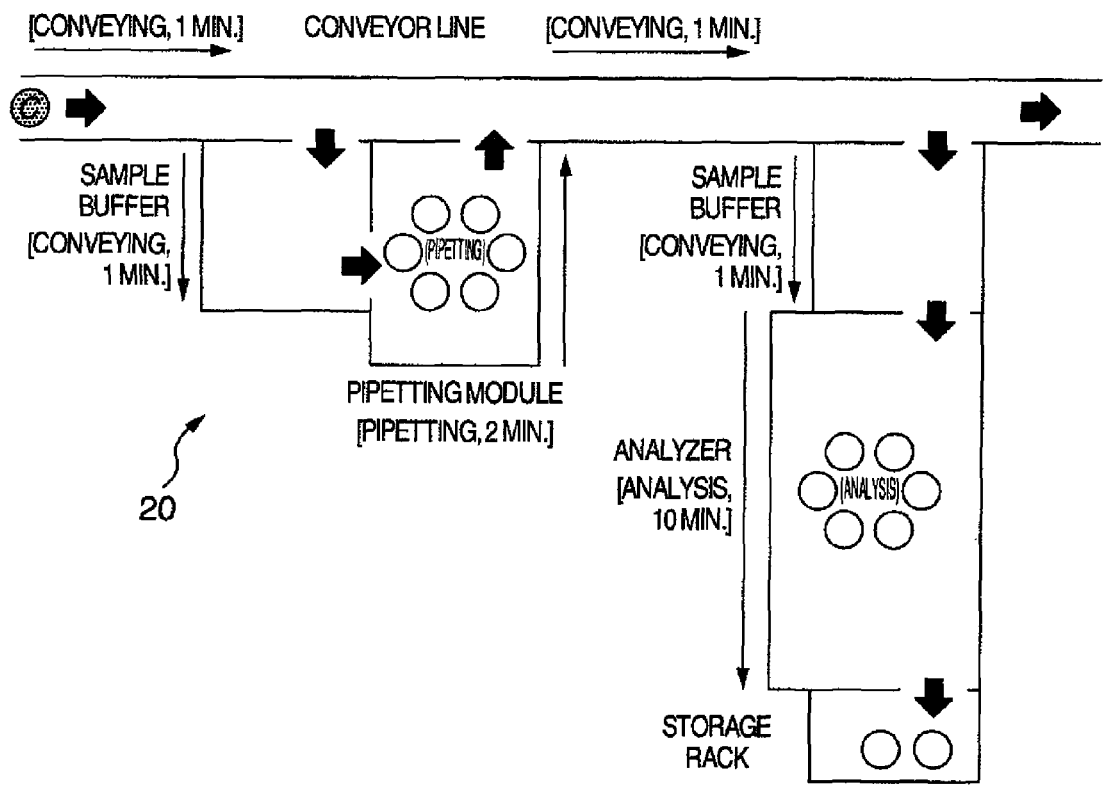
FIGS. 4A and 4B are process charts each showing a simulation process corresponding to the priority of the sample inspection system according to the invention.

Referring initially to FIGS. 4A and 4B, the simulation management portion 35 calculates the required time of the sample inspection corresponding to the processing capacity of the sample inspection line 20 set by the facility data 80 irrespective of the priority provided that no sample flows ahead of the sample charged into the sample inspection line 20. For example, the simulation management portion 35 calculates for the sample having the priority of the level C in such a fashion that one minute is necessary in the conveyor path to the sample buffer, another one minute in the sample buffer, two minutes for the work in the pipetting module, one minute in the conveyor path to the next sample buffer, another one minute in the sample buffer and 10 minutes for the work for the analyzing module. In other words, the simulation management portion 35 calculates that the required time is 16 minutes irrespective of the priority unless a sample or samples flow ahead.

When the sample flows ahead as shown in FIGS. 5A to 7B, on the other hand, the simulation management portion 35 calculates the required time corresponding to the priority. This process will be explained concretely with reference to the priority of the sample 1 flowing afterward. Here, the explanation will be given on the case where the sample 2 having the priority of the level B and the sample 3 having the priority of the level C are under the waiting state in the sample buffer of the pipetting module and the samples 4 and 5 having the priority of the level C and the sample 6 having the priority of the level B are under the waiting state in the sample buffer of the analyzing module. It will be assumed further that the pipetting module has the processing capacity of six samples and needs the waiting of 2 minutes, and the analyzing module has the processing capacity of six samples and the samples can be charged with the interval of 3 minutes.

Figures 5A, 5B:
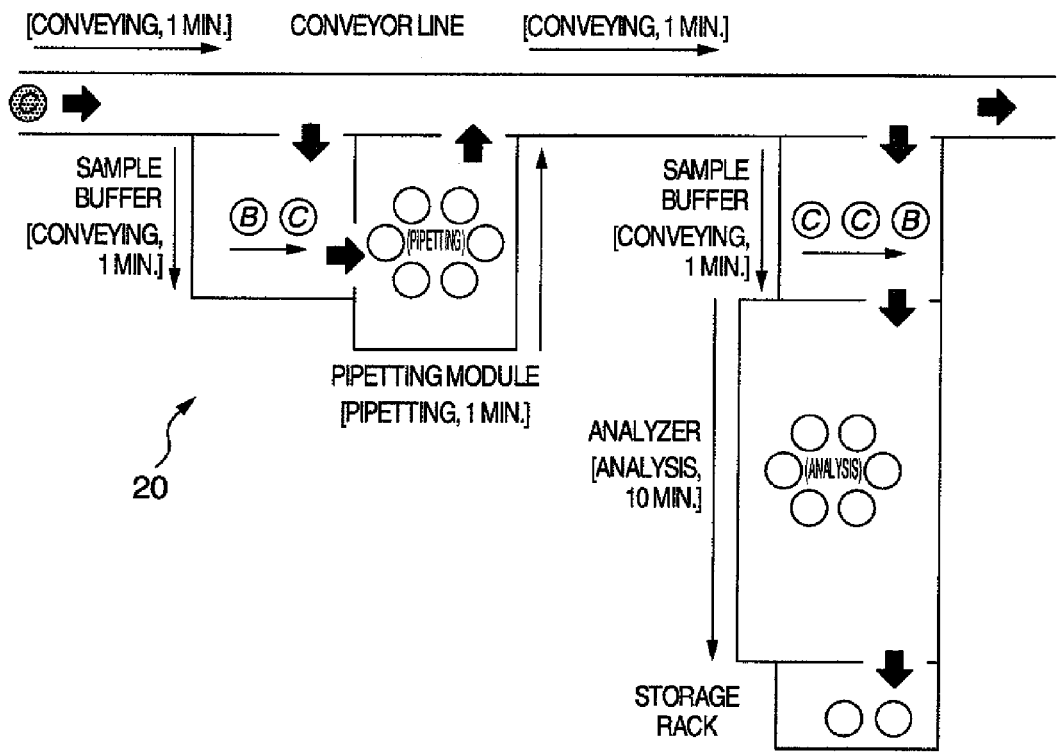
FIGS. 5A and 5B are process charts each showing a simulation process corresponding to the priority of the sample inspection system according to the invention.

Referring to FIGS. 5A and 5B, overrun of the samples does not occur when the sample 1 flowing afterward has the priority of the level C. Therefore, the samples flow in the sequence of the samples waiting inside the sample buffer.

Therefore, the waiting time of 6 minutes is necessary in the sample buffer of the pipetting module before the inspection of the samples 2 and 3 is finished. Similarly, the waiting time of 9 minutes is necessary in the sample buffer of the analyzing module. As a result, the required time of 31 minutes is necessary when the sample 1 has the priority of the level C and the delay of 15 minutes is calculated as occurring.

The samples 2 to 6 are not affected by the sample of the level C. However, they overrun the sample of the level C, since the samples 2 and 6 have the level B. In this case, the sample 2 of the level B overruns the sample 3 of the level C of the pipetting module and also overruns the sample 4 of the level C that is about to be put to the analyzing work in the sample buffer of the pipetting module.

Incidentally, FIG. 5B represents the influences of the required time on other samples by charging of the sample 1. In practice, however, the simulation management portion 35 simulates the required time from the start till the end of each sample as in the case of the sample 1.

Figures 6A, 6B:
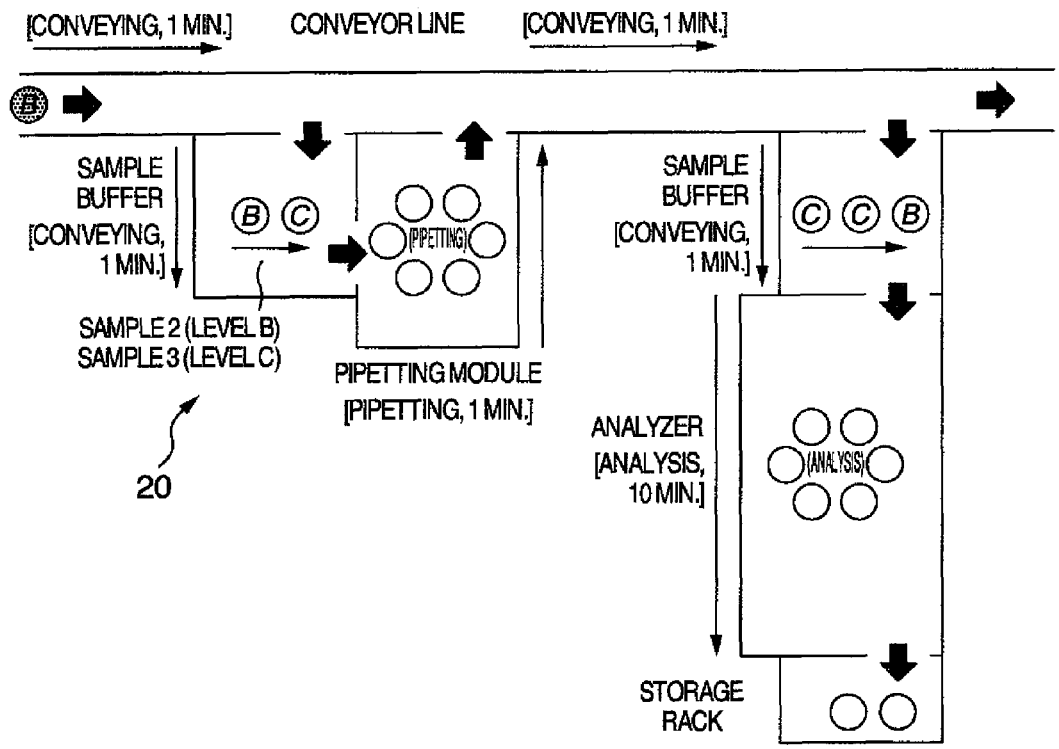
FIGS. 6A and 6B are process charts each showing a simulation process corresponding to the priority of the sample inspection system according to the invention.

Next, FIGS. 6A and 6B show the case where the sample 1 has the priority of the level B. Other samples 2 to 6 are the same as those shown in FIGS. 5A and 5B. The sample 1 of the level B overruns the sample 3 of the level C in the sample buffer of the pipetting module and follows the sample B of the level B. In the sample buffer of the analyzing module, the sample 1 overruns the sample 4 of the level C that is about to be put to the analyzing work in succession to the sample 2 of the level B. As a result, the required time of 21 minutes is necessary when the sample 1 has the level B and the delay of 7 minutes is calculated as occurring. As for other samples, it can be understood that the sample 3 of the level C is further delayed by 2 minutes and the sample 4, by 3 minutes, as the sample 1 of the level B is charged.

Figures 7A, 7B:
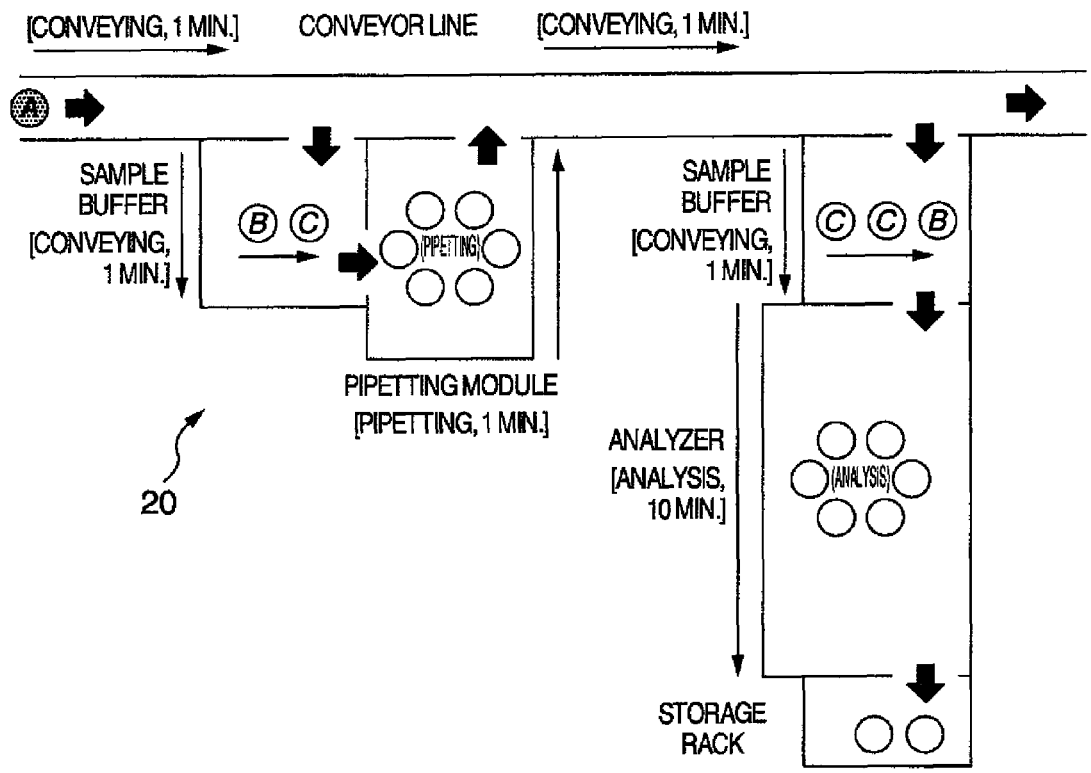
FIGS. 7A and 7B are process charts each showing a simulation process corresponding to the priority of the sample inspection system according to the invention.

Next, FIGS. 7A and 7B show the case where the sample 1 has the priority of the level A. Other samples 2 to 6 are the same as those shown in FIGS. 5A and 5B. The sample 1 of the level A overruns the samples 2 and 3 of the levels B and C in the sample buffer of the pipetting module and also overruns the samples 4 and 5 of the level C that are about to enter the analyzing work in the sample buffer of the analyzing module. As a result, the required time is calculated as 16 minutes when the sample 1 has the level A and no delay occurs. As for other samples, the samples 2 and 3 of the levels B and C are further delayed by 2 minutes and the samples 4 and 5 of the level C, by 6 minutes, as the sample 1 of the level A is charged.

As described above, this embodiment can finish quickly the inspection work by setting the priority of the samples charged later to a higher priority. As is obvious from the simulation result described above, however, great influences are exerted on the required time of other samples that are charged beforehand when the priority of the samples charged later is set to a higher level. In other words, the causes of the delay become greater when the overrun of the samples occurs more frequently among the samples.

In this embodiment, therefore, the monitor window 100 capable of monitoring the priority processing while taking the priorities of a plurality of samples processed inside the sample inspection line 20 and the progress of processing into account is provided to the local terminal 40 that monitors and controls the sample inspection line 20. This monitor window will be explained with reference to FIG. 8.

Figure 8:
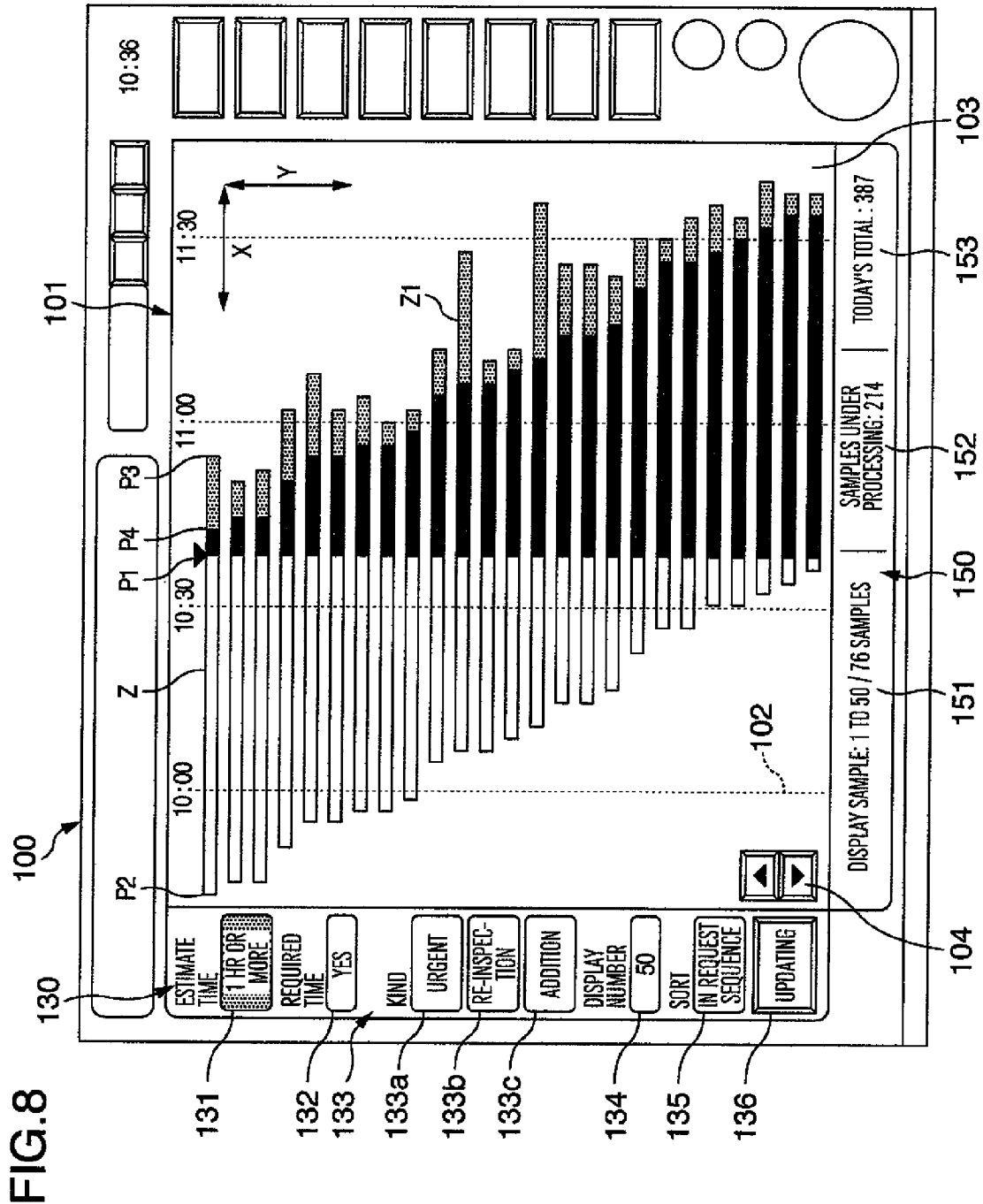
FIG. 8 shows a monitor window displayed by a display device of a local terminal of the sample inspection system according to the invention.

FIG. 8 shows the monitor window 100 displayed on the display device 42 of the local terminal 40. The monitor window 100 is the one that is generated by the management server 30. The local terminal 40 can execute the input operation by operating a keyboard 43 and a mouse 44 while monitoring the monitor window 100 generated by the management server 30.

This monitor window 100 includes a work area 101 for displaying the sample bars Z, a selection area 130 for retrieving the sample bars Z displayed in the work area 101, an operation management display area 150 and a work display area 170.

The work area 101 is a main display area of a bar graph type in which the abscissa represents the time axis X and the ordinate Y does the sample. The present time P1 is set to the center of the abscissa X. The left side as one of the sides of the present time P1 is a past record area 102 and the right side as the other side is an estimate area 103. Each sample is represented along the abscissa X by the sample bar Z that is transversely elongated. A plurality of samples each represented by the sample bar Z is aligned in the vertical direction along the ordinate Y.

Each sample bar Z represents the length from the inspection start time P2 to the estimate time P3 (estimated finish time) of the finish of the inspection with the present time P1 as the center. The sample bars Z represent distinguishably the past record area 102 and the estimate area 103 by distinguishable colors and patterns. Furthermore, the required time P4 is displayed on each sample bar Z. The time from this required time P4 to the estimate time P3 of the finish of the work is defined as the delay time Z1 and is displayed distinguishably by other colors and patterns.

Incidentally, the delay time Z1 is calculated by the inspection start time P2 in the embodiment described above but may also be set by the difference between the ordered time and the estimate time P3 of the finish of the work. The sample bar Z may also be displayed from the ordered time.

In the embodiment described above, the start time is transmitted to the management server after the pipetting processing of the sample to the slave samples is executed. This start time can be set to any of the sampling time of the sample, the order time of the inspection request, the acceptance time in the consultation room, the charging time of the sample into the pre-processor and the actual starting time of the inspection.

Furthermore, the required time may be the time that is in advance decided in accordance with the inspection requesting party of the sample. For example, the required time may be set in advance to 11:00 a.m. when the inspection requesting party is a health screening center, and to 1 hour from the order when the inspection requesting party is an outpatient clinic, and to 4:00 p.m. when the inspection requesting party is a hospitalization ward etc. In this way, the required time need not be set whenever the inspection request is generated.

As for the calculation of the delay time, the delay time can be calculated by first calculating the inspection estimate finish time from the standard processing time based on the past statistic data and the time at which the sample passes by a predetermined position of the sample inspection system and then determining the difference from the required time.

On the other hand, various kinds of operation buttons for setting the display condition of the sample bars Z displayed in the work area 101 and for switching the display content are displayed in the selection area 130. The operator can give the operation instruction by setting the cursor to the operation button and executing a determination operation. The selection area 130 includes an estimate time button 131 for setting the estimate time from the present time P1 to the estimate time P3 to the finish of the work, a required time button 132 for setting the range of the required time P4, a sample kind button 133, a display number button 134 for selecting the number of the samples (sample bars) to be displayed in the work area 101, a sort button 135 for selecting the sort of the samples (sample bars) to be displayed in the work area 101 and an updating button 136 for executing retrieval in the retrieval condition.

A case list element is displayed in a pull-down display when the cursor is put to each button other than the updating button 136 and one of these buttons can be selected. The estimate time button 131, for example, can be selected from the case list elements such as the estimate time of at least 30 minutes from the present time P1 to the estimate finish time P3 of the work, the estimate time of at least one hour, and so forth. The required time button 132 can be selected from YES, NO and Designated Time. The display number button 134 can be selected from the display number and the sort button 135, from the sequence of request and the priority.

Incidentally, when the samples (sample bars) cannot be displayed fully in the work area 101 by the selection of the display number button 134, the management server 30 displays the scroll button 104 of the Y axis in the work area 101. The sample kind button 133 includes an urgent button 133$a$ for selecting the priority, a re-inspection button 133$b$ for selecting re-inspection and an addition button 133$c$ for selecting an additional sample.

Receiving the retrieval condition designated by the estimate time button 131, the required time button 132 and the sample kind button 133, the management server 30 executes this designated retrieval, generates the result as a bar graph of the work area 101 and displays it on the monitor screen 100 of the display device 42 of the local terminal 40.

The operation management display area 150 includes a display sample portion 151 for representing the retrieval number of the samples retrieved in response to the retrieving condition and the range of the samples (sample bars) displayed in the work area 101 in response to the display number button 134, an under-processing sample portion 152 for representing the number of samples (sample bars) that are now processed and an accumulation portion 153 for today for representing the number of samples processed up to now today by the sample inspection system 1$a$.

It becomes possible by using this monitor window 100 to visually grasp the processing result and the expected processing result of a plurality of samples under processing as one bar graph group with the present time P1 as the center. Moreover, each sample expressed as the sample bar Z is expressed as a bar graph that connects the starting time P2 to the estimate finish time P3 of the work and this bar graph is displayed in such a fashion as to correspond to the time axis X. Therefore, the inspection condition can be grasped visually easily. The delay condition of each sample can be grasped more easily in connection with the condition of other samples, since the delay time Z1 is displayed at the same time.

The work area 101 capable of easily monitoring the condition and the selection area 130 in which the group of operation buttons for switching the retrieval and display of the samples (sample bars) displayed in this work area 101 are arranged in concentration are simultaneously displayed on the monitor window 100. Therefore, the retrieval condition and display can be switched while the operator confirms the retrieval result. The operator can confirm the overall condition while executing the operation management of the samples, since the monitor window 100 includes the operation management display area 150 and the work display area 170.

Next, the operation of the monitor window 100 will be explained in further detail with reference to FIG. 1 and window transition diagrams of FIGS. 8 and 10A on the basis of the operation flowchart of the monitor window 100 shown in FIG. 9. Here, FIG. 9 is an operation flowchart of the monitor window 100 and FIG. 10A is a window transition diagram of the monitor window 100.

Figure 9:
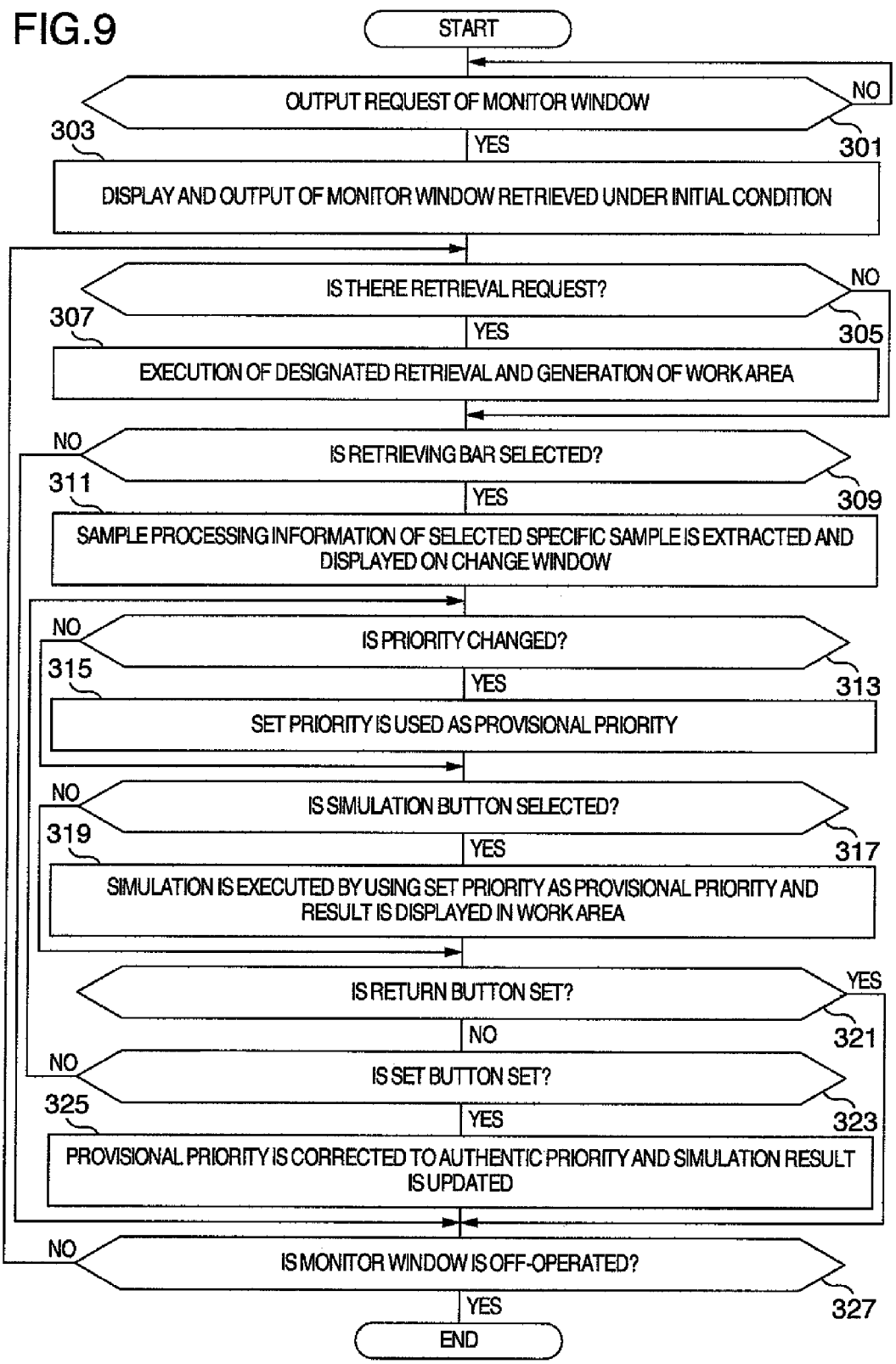
FIG. 9 is an operation flowchart of the monitor window of the sample inspection system according to the invention.
Figure 10A:
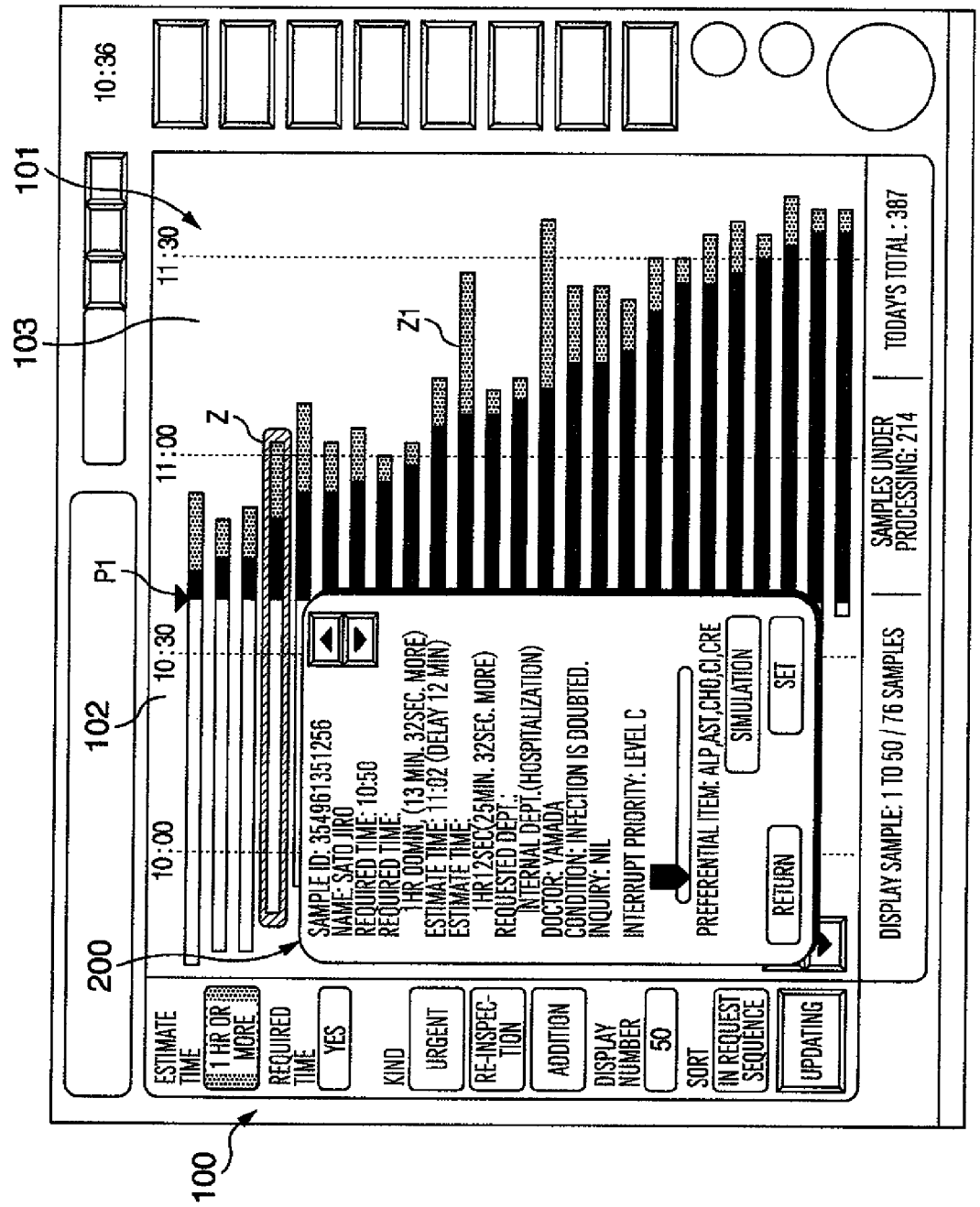
FIGS. 10A and 10B show a monitor window displayed by the display device of the local terminal of the sample inspection system according to the invention.

Referring initially to FIG. 9, the management server 30 manages the operation of the sample inspection in the sample inspection system 1a and generates the monitor window 100 as its monitor window. The management server 30 monitors the output request from the local terminal 40 (step 301). When the request exists, the monitor window 100 is outputted to the display device 42 of the local terminal 40 (step 303). The monitor window 100 so outputted outputs the sample extracted on the basis of the retrieval condition set by initial setting.

After outputting the monitor window 100, the management server 30 monitors whether or not the estimate time button 131 and the required time button 132 provided to the selection area 130 are operated (step 305), whether or not the retrieval bar Z of the specific sample is selected (step 309) and whether or not the OFF operation of the monitor window is made (step 327). When the retrieval request exists in step 305, retrieval of the sample is executed under the corresponding retrieval condition and the sample so retrieved is displayed as a sample bar Z group in the work area 101.

Figure 10B:
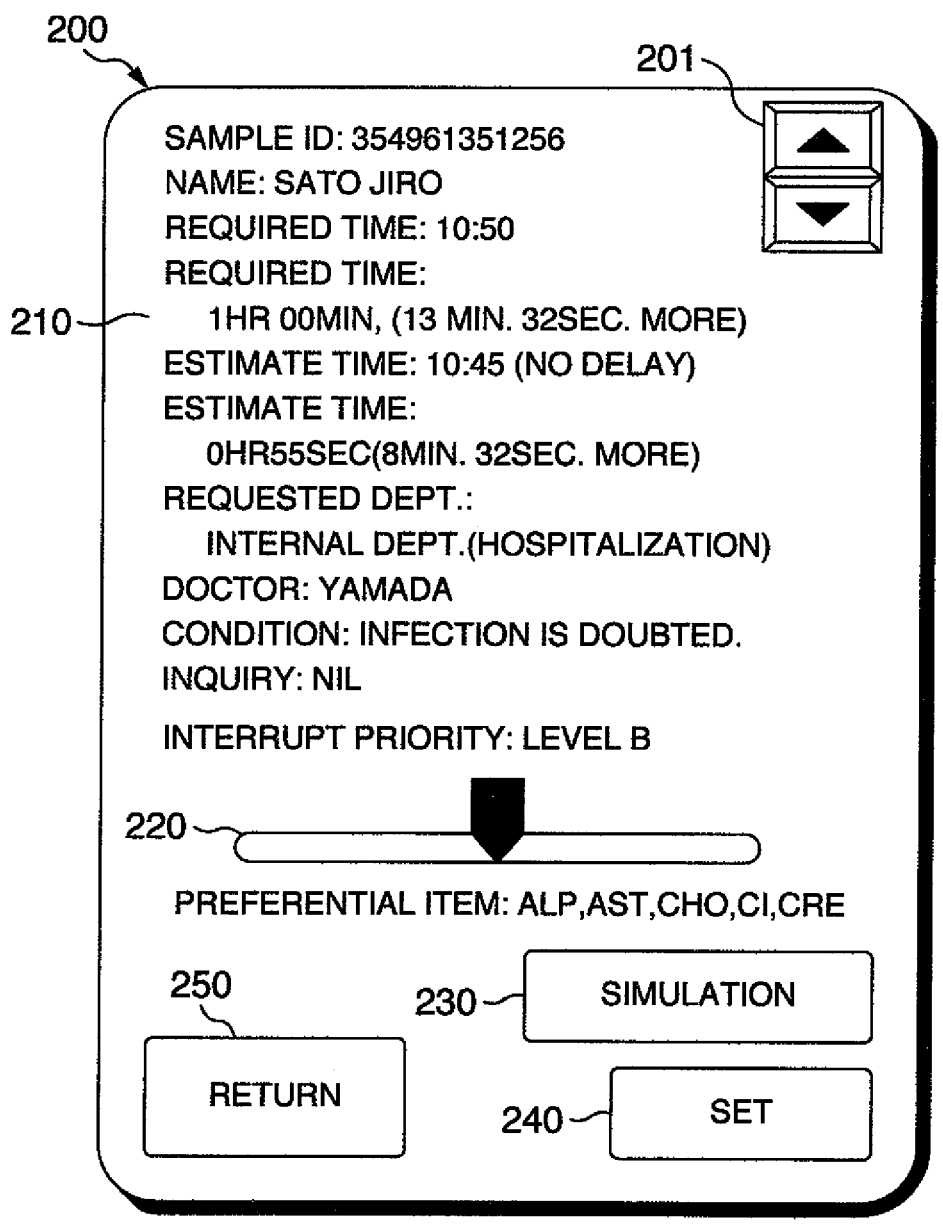

When the sample bar Z of the specific sample is selected in step 309, the sample processing information 70 of the specific sample selected and its associated information are acquired and are displayed on the change window 200 that is displayed in superposition on the monitor window 100 (step 311). FIG. 10B shows this change window 200.

The change window 200 is displayed on the past area 102 as initialization so as not to deteriorate visibility of the work estimate area 103. Needless to say, the change window 200 can be operated as an ordinary pop window through a mouse operation. Selection of a certain specific operation can be accepted through activation by a double click operation of one sample bar Z. The sample bar Z can be dragged in the interlocking arrangement with the shift key operation of the keyboard 43 or a plurality of sample bars Z can be selected arbitrarily. A page key 201 is provided to the change window 200 for this purpose.

An identification information display portion 210 for displaying the sample processing information 70 and its associated information, a priority change portion 220, a simulation button 230, a setting button 240 and a return button 250 are provided to the change window 200.

The identification information display portion 210 in this embodiment displays a sample ID, a patient's name, a required time representing an absolute time requiring the inspection result, a required time representing a relative lapse of time from the order of the request of the inspection result and the remaining time from the present time represented inside the parenthesis, an estimate time representing the delay time obtained by comparing the absolute time at which the output of the inspection result is expected with the required time represented inside the parenthesis, an estimate time representing the relative time lapsed from the order at which the output of the inspection result is expected and remaining time from the present time represented inside the parenthesis and information effective for judging the priority such as a doctor in charge and a patient's condition.

The priority change portion 220 is a setting button of a slide type and a provisional priority can be changed by the movement of this slide button, as shown in FIG. 10B. The simulation button 230 is an operation button for allowing the simulation management portion 35 to execute simulation. The setting button 240 is the one that accepts the provisional priority set by the priority setting portion 220 as the authentic priority. The return button 250 is a cancel button.

The page key 201 is a switch button for selecting and switching the display inside the change window 200 from a plurality of samples selected. When a plurality of samples is selected, the simulation button 230 and the setting button 240 are regarded as being operated for all the selected samples.

Turning back again to FIG. 9, when the change operation is made in step 311, the management server 30 monitors whether or not the priority is selected (step 313), whether or not the simulation button 230 is selected (step 317), whether or not the return button 250 is selected (step 321) and whether or not the setting button 240 is selected (step 323).

When the priority is selected in step 313, the set priority is set as the provisional priority (step 315). When the simulation button 230 is selected in step 317, the simulation management portion 35 is allowed to execute simulation on the basis of the provisional priority and the simulation result is reflected on the work area (step 319). When the return button 250 is selected in step 321, the flow proceeds to step 327. When the setting button 240 is selected in step 323, the provisional priority is set as the authentic priority and the simulation result is updated as the data of the sample processing information 70 (step 325).

When the OFF operation of the monitor window is made in step 327, the processing is finished.

According to this embodiment, the sample inspection line 20 is monitored by the monitor window 100 and samples having a serious delay can be caught easily. Moreover, the priority can be changed while the influence of the change of a specific sample is grasped by easily designating such a specific sample while watching the inspection condition of each sample.

Incidentally, though the embodiment given above deals with the case where each sample has the priority, the invention is not particularly limited thereto. For instance, it is possible to employ and operate a system in which only urgent samples are designated as the specific sample.

As described above, the sample inspection system according to this embodiment executes the sample inspection by connecting the sample inspection line, the management server, the sample access system and the monitor device of the management server through the network. The management server includes the sample processing information generated on the basis of the inspection request data accepted from the sample access system, the facility data having a processing time of the sample inspection line, the simulation execution portion for simulating the processing time of the sample on the basis of the sample processing information and the facility data and the window generation portion for generating the monitor window to be outputted to the monitor device; the inspection request data includes the patient ID, the priority, the order time, the required time and the inspection items; the sample processing information contains the inspection start time and the inspection estimate finish time in addition to the information of the inspection request data; the monitor window includes the work area for vertically arranging the samples represented by the sample bars parallel to the abscissa to which the past record and the future schedule are allocated with the present time as the base; the sample bars display the inspection start time, the inspection estimate finish time, and the delay time determined from the required time and the inspection estimate finish time; and the management server displays the simulation result processed by the simulation execution portion on the monitor window.

In this case, the monitor window includes the selection area for setting the retrieval condition of the samples on the basis of the sample processing information, and the management server executes retrieval under the retrieval condition accepted in the selection area and displays the sample extracted by this retrieval in the work area. Further, the management server accepts the selection designating the sample bar, displays the sample processing information of the sample relating to the selected sample bar inside the window displayed in superposition on the work area, executes simulation based on the provisional priority on the basis of operations of the setting portion for the provisional priority arranged inside the window, the simulation start switch and the setting switch for setting the provisional priority to the authentic priority, and executes the processing for converting the provisional priority to the authentic priority.

The information displaying method for the management server for controlling the operation of the sample inspection system for executing sample inspection according to this embodiment involves the steps of accepting inspection request data containing the patient ID, the priority, the order time, the required time and the inspection items from the sample access system; generating the sample processing information containing the inspection start time and the inspection estimate finish time in addition to the information of the inspection request data and storing the inspection processing information in the storage device; simulating the processing time of the sample on the basis of the sample processing information and the facility data having the processing time of the sample inspection line stored in the storage device; and generating the simulation result as the monitor window to be outputted to the monitor device; wherein the monitor window has the work area for arranging vertically the samples represented by the sample bars parallel to the abscissa to which the past record and the future schedule are allocated with the present time as the base; wherein the sample bar displays the inspection start time, the inspection estimate finish time and the delay time determined from the required time and the inspection estimate finish time; and wherein the monitor window is outputted to the monitor device on the basis of the request from the monitor device.

In the information displaying method in this case, the monitor window includes the selection area for setting the retrieval condition of the sample on the basis of the sample processing information; and the management server executes the retrieval under the retrieval condition accepted in the selection area and displays the sample extracted by the retrieval in the work area. In the information displaying method in this case, the management server accepts the selection designating the sample bar and displays the sample processing information of the sample relating to the selected sample bar in the window displayed in superposition on the work area, executes simulation based on the provisional priority on the basis of operations of the setting portion of the provisional priority disposed inside the window, the simulation start switch and the setting switch for setting the provisional priority to the authentic priority, and executes the processing for converting the provisional priority to the authentic priority.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A sample inspection system for executing sample inspection, comprising:
   a sample inspection line to inspect each sample of a plurality of samples;
   a management server;
   a sample access system; and
   a monitor device of the management server;
   wherein the sample inspection line, the management server, the sample access system, and the monitor device of the management server, are connected via a network;
   wherein the management server is configured to include, for each sample of the plurality of samples, sample processing information generated on a basis of inspection request data accepted from the sample access system, and to include facility data having a processing time of the sample inspection line, and is configured to simulate, for said each sample of the plurality of samples, an inspection estimate finish time for said each sample based on the sample processing information and the facility data, to obtain simulation results for the plurality of samples, respectively;
   wherein the inspection request data, for said each sample, contains a patient identification (ID), a priority corresponding to the sample, an order time, a required time and inspection items;
   wherein the sample processing information contains an inspection start time in addition to the information of the inspection request data;
   wherein the management server is configured to generate a monitor window to include a work area concurrently illustrating, for said each sample of the plurality of samples, an individual sample-bar representation, respectively, where a collection of sample-bar representations are arranged side-by-side with respect to each other and parallel to an axis of a sample-bar representation chart, and each individual sample-bar representation includes a past record portion and a future schedule portion, with a present time used as a reference time;
   wherein the sample-bar representations display, for each of the plurality of samples: the inspection start time, the inspection estimate finish time, and the delay time determined from a difference between the required time and the inspection estimate finish time; and
   wherein the management server is configured to display the work area concurrently illustrating an individual sample-bar representation of said each sample of the plurality of samples, respectively, on the monitor window.

2. A sample inspection system according to claim 1, wherein the monitor window includes a selection area for setting a retrieval condition of the samples on the basis of the sample processing information; and wherein the management server is configured to execute retrieval under the retrieval condition accepted in the selection area and to display the sample extracted by this retrieval in the work area.

3. A sample inspection system according to claim 1, wherein the management server is configured to: display the sample processing information on the past record portion, accept a selection designating a selected sample-bar representation, display the sample processing information of the sample relating to the selected sample-bar representation in a window displayed in superposition on the work area, execute simulation based on a provisional priority on the basis of operations of a setting portion of the provisional priority disposed inside the window, a simulation start switch and a setting switch for setting the provisional priority to a set priority, and execute a processing for converting the provisional priority to the set priority.

4. A sample inspection system according to claim 2, wherein the management server is configured to: accept a selection designating a selected sample-bar representation, display the sample processing information of the sample relating to the selected sample-bar representation inside the window displayed in superposition on the work area, execute simulation based on a provisional priority on the basis of operations of a setting portion for the provisional priority arranged inside the window, a simulation start switch and a setting switch for setting the provisional priority to a set priority, and execute a processing for converting the provisional priority to the set priority.

5. A sample inspection system according to claim 1, wherein the management server is configured to generate the delay time for a sample, by first calculating the inspection estimate finish time from a standard processing time based upon past statistic data and a time at which the sample passes by a predetermined position of the sample inspection system, and then the delay time is obtained by comparing the required time and the inspection estimate finish time.

6. An information displaying method effected in a sample inspection system for executing sample inspection, which includes:
   a sample inspection line to inspect each sample of a plurality of samples;
   a management server;
   a sample access system; and
   a monitor device of the management server;
   wherein the sample inspection line, the management server, the sample access system, and the monitor device of the management server, are connected via a network;
   the information displaying method comprising:
   maintaining, via the management server for each sample of the plurality of samples: sample processing information generated on the basis of inspection request data accepted from the sample access system, facility data having a processing time of the sample inspection line, a simulation simulating, for said each sample of the plurality of samples, an inspection estimate finish time for said each sample based on the sample processing information and the facility data, and a monitor window to be outputted to the monitor device;
   wherein the inspection request data, for said each sample, contains a patient identification (ID), a priority corresponding to the sample, an order time, a required time and inspection items;
   wherein the sample processing information contains an inspection start time in addition to the information of the inspection request data;
   wherein the management server generates the monitor window to include a work area concurrently illustrating, for said each sample of the plurality of samples, an individual sample-bar representation, respectively, where the work area includes a collection of sample-bar representations arranged side-by-side with respect to each other and parallel to an axis of a sample-bar representation chart, and each individual sample-bar representation includes a past record portion and a future schedule portion, with a present time used as a reference time;
   wherein the sample-bar representations display, for each of the plurality of samples: the inspection start time, the inspection estimate finish time, and the delay time determined from a difference between the required time and the inspection estimate finish time;

the information displaying method further comprising:
   displaying the work area concurrently illustrating the individual sample-bar representation of said each sample of the plurality of samples, respectively, on the monitor window; and
   accepting a selection designating a selected sample-bar representation, executing simulation based on a user-selected provisional priority, receiving an acceptance for setting the provisional priority to a set priority, and responsive to the acceptance, executing a processing for converting the provisional priority to the set priority.

7. An information displaying method for a management server according to claim 6, wherein the information displaying method comprises: accepting the selection designating the sample-bar representation, displaying the sample processing information of the sample relating to the selected sample-bar representation in a priority window displayed in superposition on the work area, executing the simulation based on a provisional priority on the basis of operations of a setting portion of the provisional priority disposed inside the priority window, a simulation start switch and a setting switch for setting the acceptance of the provisional priority to the set priority, and executing the processing for converting the provisional priority to the set priority.

8. An information displaying method for a management server according to claim 6, wherein the monitor window includes a selection area for setting a retrieval condition of the sample on the basis of the sample processing information; and
   wherein the information displaying method comprising executing retrieval under the retrieval condition accepted in the selection area, and displaying the sample extracted by the retrieval in the work area.

9. An information displaying method for a management server according to claim 8, wherein the information displaying method comprises: displaying the sample processing information on the past record portion, accepting the selection designating the sample-bar representation, displaying the sample processing information of the sample relating to the selected sample-bar representation in a priority window displayed in superposition on the work area, executing the simulation based on a provisional priority on the basis of operations of a setting portion of the provisional priority disposed inside the priority window, a simulation start switch and a setting switch for setting the acceptance of the provisional priority to the set priority, and executing the processing for converting the provisional priority to the set priority.

10. An information displaying method for a management server according to claim 6, further comprising generating the delay time for a sample, by first calculating the inspection estimate finish time from a standard processing time based upon past statistic data and a time at which the sample passes by a predetermined position of the sample inspection system, and then obtaining the delay time by comparing the required time and the inspection estimate finish time.

11. A sample inspection system for executing sample inspection, comprising:
   a sample inspection line to inspect each sample of a plurality of samples;
   a management server;
   a sample access system; and
   a monitor device of the management server;
   wherein the sample inspection line, the management server, the sample access system, and the monitor device of the management server, are connected via a network;
   wherein the management server is configured to include, for each sample of the plurality of samples, sample processing information generated on a basis of inspection request data accepted from the sample access system, and to include facility data having a processing time of the sample inspection line, and is configured to simulate, for said each sample of the plurality of samples, an inspection estimate finish time for said each sample based on the sample processing information and the facility data, to obtain simulation results for the plurality of samples, respectively;

wherein the inspection request data, for said each sample, contains a patient identification (ID), a priority corresponding to the sample, an order time, a required time and inspection items;

wherein the sample processing information contains an inspection start time in addition to the information of the inspection request data;

wherein the management server is configured to generate a monitor window to include a work area concurrently illustrating, for said each sample of the plurality of samples, an individual sample-bar representation, respectively, where a collection of sample-bar representations are arranged side-by-side with respect to each other and parallel to an axis of a sample-bar representation chart, and each individual sample-bar representation includes a past record portion and a future schedule portion, with a present time used as a reference time;

wherein the sample-bar representations display, for each of the plurality of samples: the inspection start time, the inspection estimate finish time, and the delay time determined from a difference between the required time and the inspection estimate finish time;

wherein the management server is configured to display the work area concurrently illustrating an individual sample-bar representation of said each sample of the plurality of samples, respectively, on the monitor window; and wherein the management server is further configured to: accept a selection designating a selected sample-bar representation, execute simulation based on a user-selected provisional priority, receive an acceptance for setting the provisional priority to a set priority, and responsive to the acceptance, execute a processing for converting the provisional priority to the set priority.

12. A sample inspection system according to claim 11, wherein the management server is configured to generate the delay time for a sample, by first calculating the inspection estimate finish time from a standard processing time based upon past statistic data and a time at which the sample passes by a predetermined position of the sample inspection system, and then the delay time is obtained by comparing the required time and the inspection estimate finish time.

13. A non-transitory computer-readable medium embodying a program for use in a sample inspection system for executing sample inspection, which sample inspection system includes:
 a sample inspection line to inspect each sample of a plurality of samples;
 a management server;
 a sample access system; and
 a monitor device of the management server;

wherein the sample inspection line, the management server, the sample access system, and the monitor device of the management server, are connected via a network;

the program, upon execution, effecting operations comprising:

maintaining, via the management server for each sample of the plurality of samples: sample processing information generated on the basis of inspection request data accepted from the sample access system, facility data having a processing time of the sample inspection line, a simulation simulating, for said each sample of the plurality of samples, an inspection estimate finish time for said each sample based on the sample processing information and the facility data, and a monitor window to be outputted to the monitor device;

wherein the inspection request data, for said each sample, contains a patient identification (ID), a priority corresponding to the sample, an order time, a required time and inspection items;

wherein the sample processing information contains an inspection start time in addition to the information of the inspection request data;

wherein the management server generates the monitor window to include a work area concurrently illustrating, for said each sample of the plurality of samples, an individual sample-bar representation, respectively, where the work area includes a collection of sample-bar representations arranged side-by-side with respect to each other and parallel to an axis of a sample-bar representation chart, and each individual sample-bar representation includes a past record portion and a future schedule portion, with a present time used as a reference time;

wherein the sample-bar representations display, for each of the plurality of samples: the inspection start time, the inspection estimate finish time, and the delay time determined from a difference between the required time and the inspection estimate finish time;

the program further effecting operations comprising:

displaying the work area concurrently illustrating the individual sample-bar representation of said each sample of the plurality of samples, respectively, on the monitor window; and accepting a selection designating a selected sample-bar representation, executing simulation based on a user-selected provisional priority, receiving an acceptance for setting the provisional priority to a set priority, and responsive to the acceptance, executing a processing for converting the provisional priority to the set priority.

14. A non-transitory computer-readable medium according to claim 13, wherein the program, upon execution, effecting further operations comprising: generating the delay time for a sample, by first calculating the inspection estimate finish time from a standard processing time based upon past statistic data and a time at which the sample passes by a predetermined position of the sample inspection system, and then obtaining the delay time by comparing the required time and the inspection estimate finish time.

* * * * *